United States Patent
Sullivan (10) Patent No.: US 6,197,024 B1
(45) Date of Patent: Mar. 6, 2001

(54) ADJUSTABLE ELECTROCAUTERY SURGICAL APPARATUS

(76) Inventor: Scott Keith Sullivan, 1022 St. Peter, #213, New Orleans, LA (US) 70116

(*) Notice: Subject to any disclaimer, the term of this patent is extended or adjusted under 35 U.S.C. 154(b) by 0 days.

(21) Appl. No.: 09/401,727

(22) Filed: Sep. 22, 1999

(51) Int. Cl.⁷ .................................................. A61B 18/18
(52) U.S. Cl. ................................. 606/45; 606/41; 606/49
(58) Field of Search ................................. 606/42, 45, 46, 606/48, 50, 39, 40, 41

(56) References Cited

U.S. PATENT DOCUMENTS

| | | |
|---|---|---|
| 1,713,971 | 5/1929 | Lowry . |
| 4,307,720 | 12/1981 | Weber . |
| 4,688,569 | 8/1987 | Rabinowitz . |
| 4,919,129 | 4/1990 | Weber . |
| 5,013,312 | 5/1991 | Parins . |
| 5,035,695 | 7/1991 | Weber . |
| 5,219,348 | 6/1993 | Buess . |
| 5,234,429 | 8/1993 | Goldhaber . |
| 5,256,138 * | 10/1993 | Burek et al. ............................ 606/42 |
| 5,273,524 | 12/1993 | Fox . |
| 5,318,565 | 6/1994 | Kuriloff . |
| 5,383,876 | 1/1995 | Nardella . |
| 5,443,462 | 8/1995 | Hannant . |
| 5,449,356 | 9/1995 | Walbrink . |
| 5,484,434 | 1/1996 | Cartmell . |

FOREIGN PATENT DOCUMENTS 4012 545   10/1991   (DE) .
543122 A1   5/1993   (EP) .

* cited by examiner

Primary Examiner—Linda C. M. Dvorak
Assistant Examiner—R. Kearney
(74) Attorney, Agent, or Firm—Shawn D. Sentilles (57) ABSTRACT

An adjustable electrocautery surgical apparatus for selectively delivering electosurgical coagulation and cut current from an electrosurgical generator to a surgical site is provided comprising an elongated body, an extension member passing at least partially through the elongated body, a track in the elongated body for guiding the extension member, an electrode blade attached to the extension member for cutting or coagulating tissue, and an adjustable lock coupled to the extension member for selectively adjusting the position of the extension member and electrode blade relative to the elongated body and for locking the extension member and electrode blade in a selected position. A longitudinal channel passes through a sidewall of the elongated body member. A plurality of stops are positioned in the channel for providing a sequence of stop positions between maximally retracted and maximally extended positions of the apparatus. The adjustable lock is slidably positioned in the longitudinal channel of the elongated body member so as to selectively engage the stops and thereby lock the electrode blade in a selected stop position between the maximally retracted and the maximally extended positions. The apparatus is further provided with means for electrically coupling the electrode blade to the coagulation and cut currents of the electrosurgical generator, such that coagulation or cut current, or a combination thereof, can be selectively delivered to the electrode blade.

23 Claims, 9 Drawing Sheets

ADJUSTABLE ELECTROCAUTERY SURGICAL APPARATUS

FIELD OF THE INVENTION

The present invention relates to electrocautery surgical instruments for use in surgical procedures, and more particularly to an adjustable electrocautery surgical instrument.

BACKGROUND OF THE INVENTION

Electrocautery surgical instruments are used to make surgical cuts and to coagulate blood along surgical cuts and around surgical sites. Electrocautery surgical instruments typically have an exposed electrode blade positioned on the lower end of an elongated body. The elongated body fits comfortably in the hand of a surgeon, and allows the surgeon to control and manipulate the electrode blade much in the manner of a conventional metal scalpel. An electric cable or cord extends from the non-cutting upper end of the elongated body. One end of the electrical cord is electrically coupled to the electrode blade, while the other end of the cord is electrically coupled to a commercially available electrosurgical generator.

Electrosurgical generators have a radio frequency oscillator circuit which delivers highvoltage, high-frequency electrical signals of various waveforms to the electrode blade to selectively sever, clamp or coagulate tissue during surgical procedures. The electrosurgical generator converts wall current (110 V, 60 Hz) into high-frequency radio waves in the range of 500,000 to 1,000,00 Hz. Electrosurgical generators typically generate two or three types ofradio frequency waves. One wave is a dampened sine wave with pure coagulating properties. Another wave is a sinusoidal wave form that has pure cutting properties. Electrosurgical generators can also generate a variable sine wave with ablended current that combines characteristics of the dampened sinusoidal and sinusoidal waves. The dampened sine wave has excellent coagulating properties, but results in marked tissue destruction and charring. The sinusoidal wave cuts through tissue with little thermal damage, much like a conventional scalpel, but has no coagulation properties. Most surgical dissection is performed with a dampened sine wave output that cuts and coagulates simultaneously with minimal thermal destruction and charring. The selection of the particular type of waveform can be regulated by a foot control pedal associated with the electrosurgical generator, or by finger controls mounted on the electrosurgical instrument. See e.g. U.S. Pat. No. 5,318,565 (Kuriloff).

Most systems for supplying the current to the electrode blade utilize a dispersive, or indifferent, electrode. The dispersive electrode is typically a large metal plate which is secured to the patient and is electrically coupled to the electrosurgical generator through a cable. The electrode blade serves as an active electrode. The high frequency current produced by the electrosurgical generator radiates from the site of tissue contact of the active electrode/ electrode blade, through the tissues of the patient to the larger indifferent electrode, back to the power oscillator of the electrosurgical generator, and then back again to the site of tissue contact of the electrode blade, in a continuing radiating cycle. The current reaches a high density at the site where the electrode blade contacts the tissue, producing cutting or coagulation. The dispersive electrode is relatively large in area, which keeps current density in the region of the dispersive electrode sufficiently low to avoid tissue burns in the patient, except where the electrode blade contacts tissue.

U.S. Pat. Nos. 4,919,129 (Weber) and 5,035,695 (Weber) disclose electrocautery surgical instruments having apartially retractable electrode blade. The surgical instruments include attachable extension units of varying lengths for selectively extending the operational utility of the instrument as a surgical procedure progresses. The extension units extend the electrode blade a selected dimension to facilitate deep surgical procedures in confined sites. A safety switch is included for controlling the application of high-voltage electrical signals to the electrode blade, and to thereby establish electrically inactive conditions during attachment and removal of extension units.

The present invention utilizes the above concepts, but applies them in a surgical apparatus which is adjustable in length through a wide range of motion.

OBJECTS AND SUMMARY OF THE INVENTION

It is an object of the invention to provide an adjustable electrocautery surgical apparatus having an extendable and retractable electrode blade.

It is another object of the invention to provide an adjustable electrocautery surgical apparatus wherein the electrode blade can be readily extended or retracted during a surgical procedure, without delaying the surgical procedure.

It is another object of the invention to provide an adjustable electrocautery surgical apparatus wherein the electrode blade can be extended and retracted over a wide range of motion.

It is another object of the invention to provide an adjustable electrocautery surgical apparatus wherein the electrode blade can be extended and retracted over a wide range of motion without requiring removal and substitution of various length electrode blades.

These and other objects and advantages of the invention shall become apparent from the following general and preferred description of the invention.

Accordingly, an adjustable electrocautery surgical apparatus for selectively delivering electrosurgical coagulation and cut current from an electrosurgical generator to a surgical site is provided comprising an elongated body, an extension member passing at least partially through the elongated body, a track in the elongated body for guiding the extension member, an electrode blade attached to the extension member for cutting or coagulating tissue, and an adjustable lock coupled to the extension member for selectively adjusting the position of the extension member and electrode blade relative to the elongated body and for locking the extension member and electrode blade in a selected position. The elongated body member has a lower end and an upper end. A longitudinal channel passes through a sidewall of the elongated body member. A plurality of stops are positioned in the channel for providing a sequence of stop positions between maximally retracted and maximally extended positions of the apparatus. The stops may be portioned in pairs on opposite sides of the channel. The stops may also be positioned on an inner surface of the elongated body on either side of the channel. A track is disposed longitudinally in the elongated body. The track is positioned substantially parallel to the channel. An elongated extension member is slidably disposed in the track. An electrode blade extends from a lower end of the extension member, with an exposed lower end of the electrode blade extending from the lower end of the elongated body. An adjustable lock is provided on the extension member. The adjustable lock is slidably positioned in the longitudinal channel of the elongated body member so as to selectively engage the stops and thereby lock the electrode blade in a selected stop position between the maximally retracted and the maximally extended positions. The apparatus is further provided with a means for electrically coupling the electrode blade to the coagulation current of the electrosurgical generator and a means for electrically coupling the electrode blade to the cut current of the electrosurgical generator, such that coagulation or cut current, or a combination thereof, can be selectively delivered to the electrode blade.

A number of adjustable lock mechanisms are provided. In a preferred embodiment, the adjustable lock comprises an engagement member for engaging the stops, a tension member for normally biasing the engagement member in a stop position, an adjustment tab for selectively disengaging the engagement member from the stops, and a guide member disposed at least partially in the channel and fixedly coupled to the adjustment tab and the extension member, such that sliding the adjustment tab causes the extension member to slide in the track to thereby selectively adjust the electrode blade between maximally extended and maximally retracted positions. In a preferred embodiment, the engagement member is on the adjustment tab, the adjustment tab is hinged to the guide member, and the tension member is positioned between the adjustment tab and the guide member so as to normally bias the engagement member in one of the stop positions. In another preferred embodiment, the extension member is provided with a cavity therein, and the engagement member and the tension member are configured from a metal strip. The tension portion of the metal strip is disposed in the cavity, and the engagement member portion of the metal strip is normally biased to protrude from an opening in the extension member so as to engage one of the stop positions. In another embodiment, the extension member has a cavity therein, the tension member is a spring positioned in the cavity, and the engagement member is a bearing, with the bearing positioned on the spring so as to normally bias the bearing in one of the stop positions. In yet another embodiment, the extension member further has a cavity therein, the engagement member is formed on a descending portion of the adjustment tab, the engagement member is positioned in the cavity of the extension member, and the tension member is positioned between the adjustment tab and the guide member so as to normally bias the engagement member in one of the stop positions.

In a preferred embodiment, the means for electrically coupling the electrode blade to the coagulation current of the electrosurgical generator further includes a coagulation circuit in the elongated body for selectively delivering coagulation current from the electrosurgical generator to the electrode blade, and the means for electrically coupling the electrode blade to the cut current of the electrosurgical generator further includes a cut circuit in the elongated body for selectively delivering cut current from the electrosurgical generator to the electrode blade. The means for electrically coupling preferably includes an electrical cord extending from the elongated body, the cord having an electric power conductor for electrically coupling with an electric power terminal of the electrosurgical generator, a coagulation switching conductor for electrically coupling with a coagulation switching terminal of the electrosurgical generator, and a cutting switching conductor for electrically coupling with a cutting switching terminal of the electrosurgical generator. The electric power conductor may be affixed to the electrode blade via a slack portion, the slack portion allowing the electric power conductor to remain in contact with the electrode blade throughout the range of adjustment of the electrode blade. The coagulation circuit may include a coagulation switch actuating means electrically coupled to the coagulation switching conductor, a biasing means for holding the coagulation switch actuating means in an open switch position when coagulation current is not required, and an external button for depressing the coagulation switch actuating means into contact with the electrode blade, to thereby close the coagulation circuit and selectively deliver electrosurgical coagulation current from the electrosurgical generator to the electrode blade. The cut circuit may include a cut switch actuating means electrically coupled to the cut switching conductor, a biasing means for holding the cut switch actuating means in an open switch position when cut current is not required, and an external button for depressing the cut switch actuating means into contact with the electrode blade, to thereby close the cut circuit and selectively deliver electrosurgical cut current from the electrosurgical generator to the electrode blade.

In another preferred embodiment, the means for electrically coupling includes an electrical cord extending from the elongated body, the cord having an electric power conductor for electrically coupling with an electric power terminal of the electrosurgical generator, a coagulation switching conductor for electrically coupling with a coagulation switching terminal of the electrosurgical generator, and a cutting switching conductor for electrically coupling with a cutting switching terminal of the electrosurgical generator. The electric power conductor is affixed to the electrode blade via a slack portion, the slack portion allowing the electric power conductor to remain in contact with the electrode blade throughout the range of adjustment of the electrode blade. The coagulation circuit includes a coagulation switch positioned between the coagulation switching conductor and a lead. The lead has a slack portion affixed to the electrode blade, the slack portion of the lead allowing the lead to remain in contact with the electrode blade throughout the range of adjustment of the electrode blade. A switch actuating means is normally biased to open the coagulation switch, and an external button for is provided for closing the coagulation circuit to selectively deliver electrosurgical coagulation current from the electrosurgical generator to the electrode blade. The cut circuit includes a cut switch positioned between the cut switching conductor and a lead, the lead having a slack portion affixed to the electrode blade. The slack portion of the lead allows the lead to remain in contact with the electrode blade throughout the range of adjustment of the electrode blade. A switch actuating means is normally biased to open the cut switch, and an external button is provided for closing the cut circuit to selectively deliver electrosurgical cut current from the electrosurgical generator to the electrode blade.

PREFERRED EMBODIMENTS OF THE INVENTION

Figure 1:
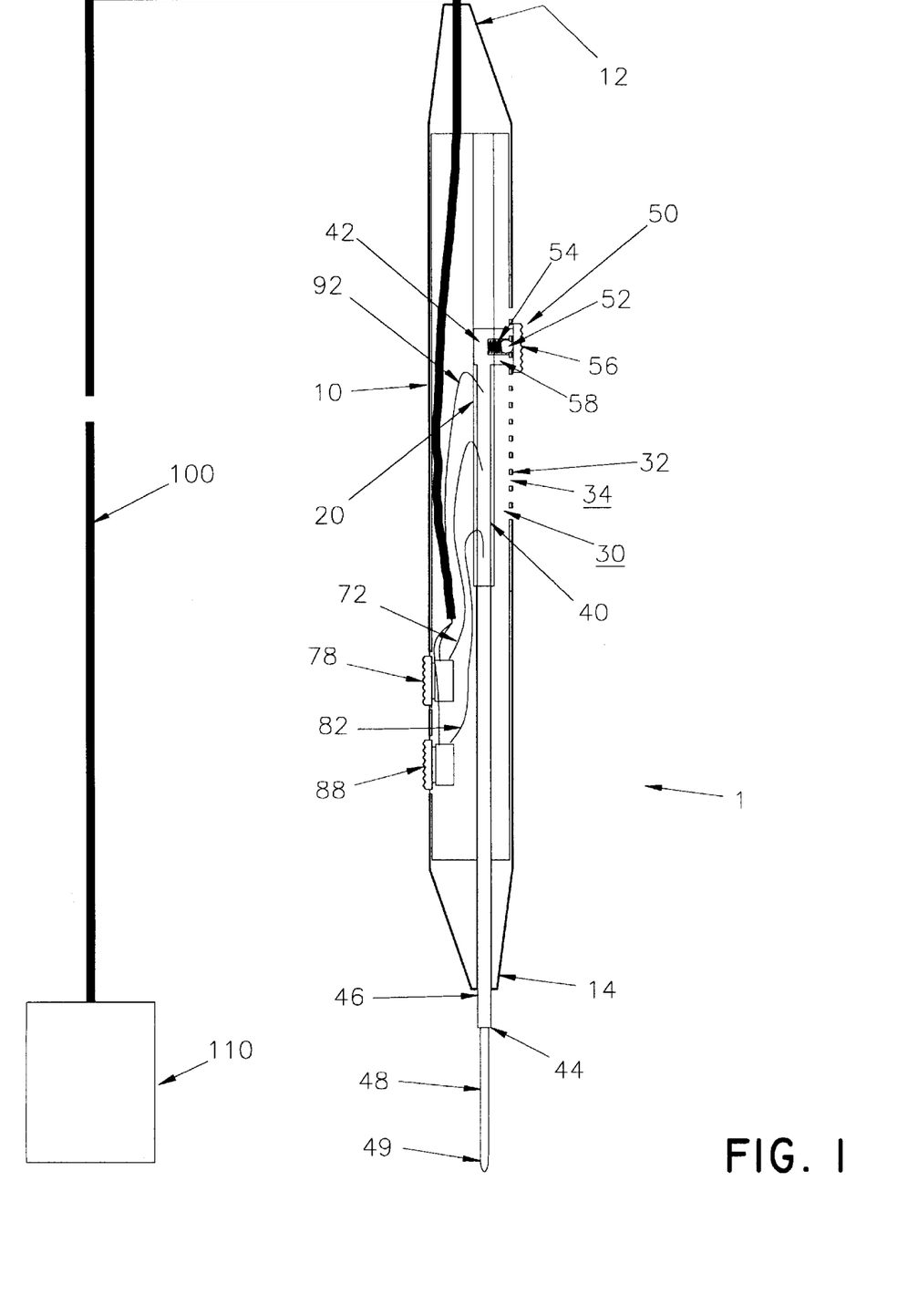
FIG. 1 is a cross-sectional side view of one embodiment of the invention illustrating the invention in a maximally retracted position.

As shown in FIG. 1, the adjustable electrocautery surgical apparatus 1 of the invention comprises, generally, an elongated body 10, an extension member 40 passing at least partially through the elongated body, a track 20 in the elongated body 10 for guiding the extension member 40, an electrode blade 48 attached to the extension member 40 for cutting or coagulating tissue, and an adjustable lock 50 coupled to the extension member 40 for selectively adjusting the position of the extension member 40 and electrode blade 48 relative to the elongated body 10 and for locking the extension member 40 and electrode blade 48 in a selected position.

Figure 2:
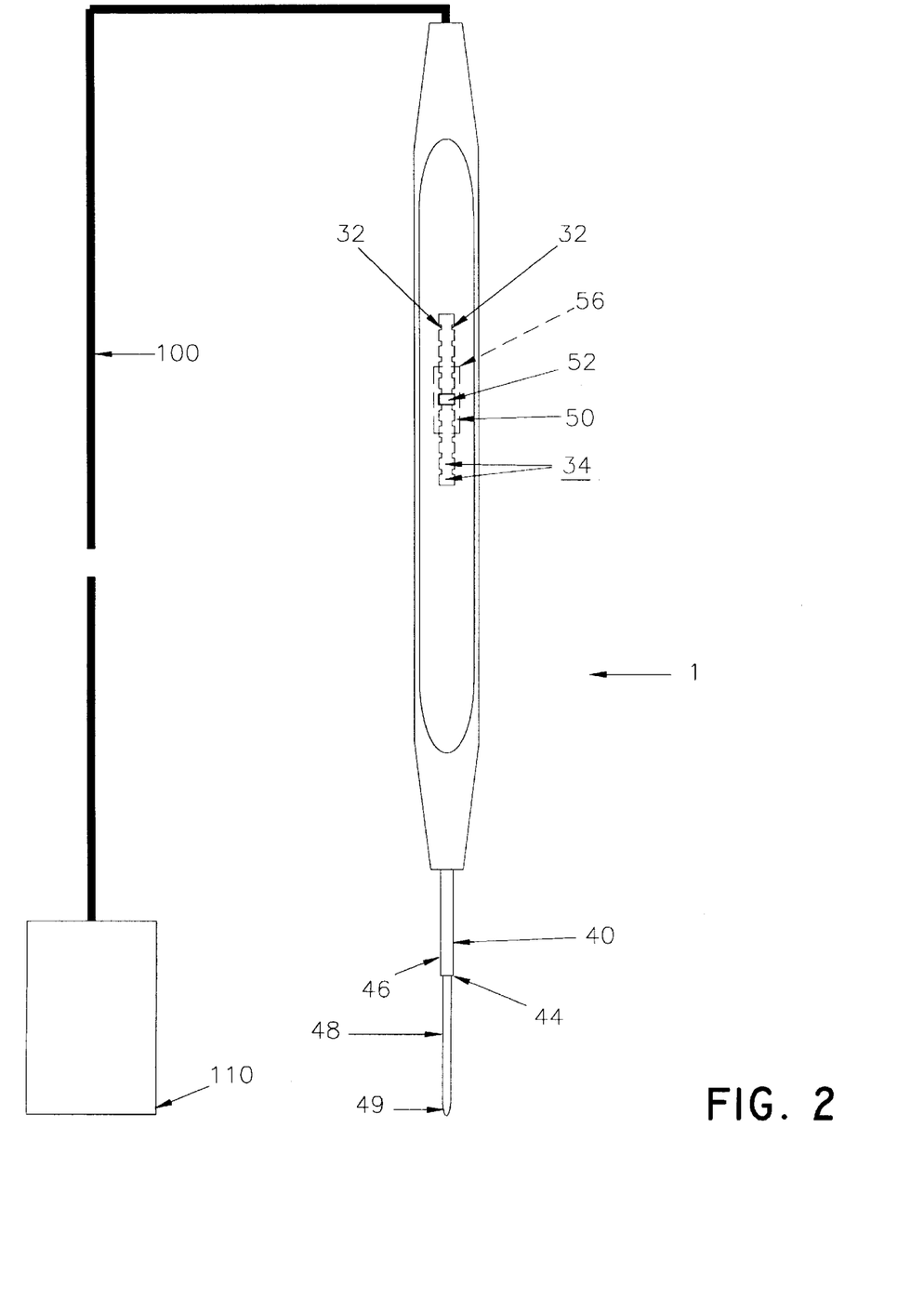
FIG. 2 is a side view of one embodiment of the invention, rotated 90 degrees from FIG. 1 and illustrating the invention in a maximally extended position.

The elongated body 10 has an upper end 12 and a lower end 14. As shown in FIG. 1, the channel 30 passes through a sidewall of the elongated body 10, and is positioned lengthwise on the elongated body 10. The channel 30 is of sufficient length to allow a desired range of extension and retraction of the extension member 40. A plurality of stops 32 are positioned in channel 30. Stop positions 34 are located between adjacent stops 32. The positioning and configuration of the stops 32 and the stop positions 34 will vary depending on the type of adjustable lock 50 employed. In a preferred embodiment, stops 32 are portioned in pairs on either side of the channel 30, as shown in FIG. 2.

For ease of construction, the elongated body 10 will typically be constructed of two halves, which are joined together to secure the various internal and external parts of the apparatus 1 in place during use. A number of cavities and passages can be configured within the elongated body 10 to accommodate the internal parts of the invention. One such cavity is the track 20, which is fixed longitudinally within elongated body 10. The track 20 is sized and configured to closely receive the extension member 40, such that the extension member 40 can be slid up and down within track 20, but such that the extension member 40 is substantially prevented from moving side-to-side within the track 20. The track 20 can also be configured to prevent the extension member from rotating axially relative to the track 20 and the body 10.

The track 20 can be formed in any of a number of shapes and configurations, provided that it guides the sliding movement of the extension member 40 in the manner described above. For example, if the extension member 40 is circular in cross-section, the track could be cylindrical, a plurality of interspersed rings, or a plurality of longitudinal tracks. If the extension member 40 is square (four-sided) in cross-section, the track could be a tube having a square cross-section, a plurality of interspersed square rings, or a plurality of longitudinal tracks.

Although many shapes and configurations can be used for the track 20, it is necessary that the track 20 have at least two longitudinal slits therein. A guide member slit (not shown) is positioned in the track 20 such that the guide member slit is substantially lined up with and parallel to the channel 30 of the body 10. As will be described further below, a guide member 58 portion of the adjustable lock 50 passes through both the guide member slit in the track 20 and the channel 30 of the body 10, thereby allowing the extension member 40 to slide within the track 20 when the adjustable lock 50 is adjusted through external manipulation of the adjustable lock 50. Additionally, an electrical slit (not shown) is positioned longitudinally in the track 20 such that certain electrical components, to be described further below, can move with or interact with the electrode blade 48 as the extension member 40 is moved up and down within the track 20.

The electrode blade 48 is affixed to the extension member 40, such that sliding the extension member 40 within the track 20 of the body will cause the electrode blade 48 to extend away from or retract toward the body 10. In a preferred embodiment, the electrode blade 48 passes substantially through the extension member 40. However, it can be appreciated that other configurations can be used, such as an electrode blade 48 which is attached only to the lower end 44 of the extension member. The extension member 40 is composed of or at least partially covered by an insulation cover or coating 46. The insulation 46 of the extension member 40 provides insulation for electrode blade 48, so that electrocautery current does not escape from the blade 48 except through an exposed lower end 49 of the blade 48. The insulation 46 of the extension member 40 is provided with holes, grooves, or other such openings as needed to permit the electrical components of the invention 1 to electrically couple with the electrode blade 48. The exposed lower portion 49 of the electrode blade 48 protrudes from the lower end 14 of the elongated body 10 of the invention 1.

The electrode blade 48 is of the type well known to those of ordinary skill in the art. The exposed lower portion 49 of the electrode blade 48 is preferably flat and has a sharp point, but it can also be configured in any of the various forms that are used on conventional electrosurgery tools, such as rounded, or in the form of a wire loop for scraping. The exposed lower end 49 of the electrode blade 48 can be coated with a non-stick coating, such as Teflon, to prevent tissue coagulum and char from adhering to it.

An adjustable lock 50 is positioned in the channel 30. The adjustable lock 50 can be configured in any of a number of configurations, as will be described in further detail below. The adjustable lock 50 has an engagement member 52 for engaging the stops 32 in the channel 30. The engagement member 52 is sized and configured to substantially fill or occupy each stop position 34, such that the extension member 40 cannot slide up and down when the adjustable lock is locked in a desired stop position 34. The adjustable lock 50 also has a spring or elastic tension member 54 for normally biasing, in the absence of an external force, engagement member 52 within the stop positions 34 between the stops 32, to thereby removably lock the extension member 40 and electrode blade 48 in a desired position. An adjustment tab 56 is providing on the adjustable lock 50 for adjusting the adjustable lock 50 between maximally extended and maximally retracted positions. The tension provided by the tension member 54 is of sufficient force to readily hold, or bias, the engagement member 52 in a selected stop position 34, and thereby selectively lock the electrode blade 48 in the selected position when the invention is used to coagulate or cut during surgical procedures. However, the tension provided by the tension member 54 is such that a surgeon can readily remove the engagement member 52 from the selected stop position 34 by applying manual pressure to the adjustment tab 56, to thereby counteract the tension force which normally biases the engagement member 52 in a stop position 34. A guide member 58 is disposed at least partially in the channel 30. The guide member 58 is fixedly coupled to the adjustment tab 56 and to the extension member 40, such that sliding the adjustment tab 56 and guide member 58 within the channel 30 causes the extension member 40 to slide in the track 20. The guide member 58 is preferably positioned at or near the upper end of the extension member 40, so as to provide a maximum range of movement of the extension member 40 relative to the lower end of the elongated body 10 of the adjustable electrocautery surgical instrument 1. The guide member 58 is configured such that it is sufficiently narrow to pass between the stops 32. The guide member 58 is also preferably sized such that the stops 32 prevent the extension member adjustable lock 50 from rotating axially within the channel 30.

As mentioned above, the adjustable lock 50 can be configured in any of a number of configurations. Several such embodiments will now be described in detail, with reference to FIGS. 5–8.

Figure 5A:
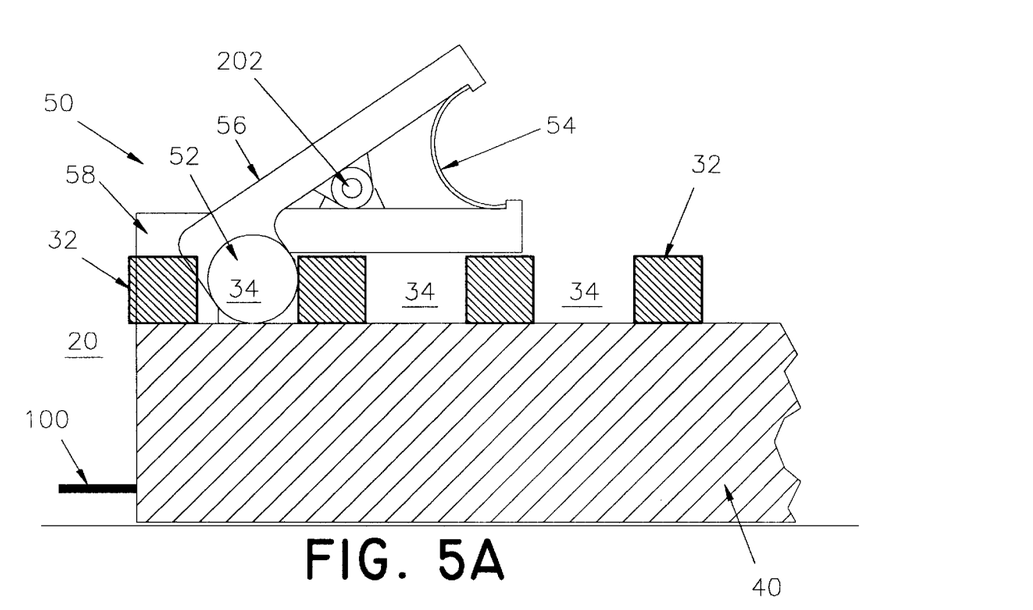
FIG. 5A is a side view of one embodiment of an adjustable lock component of the invention, illustrating the lock in an engaged position.
Figure 5B:
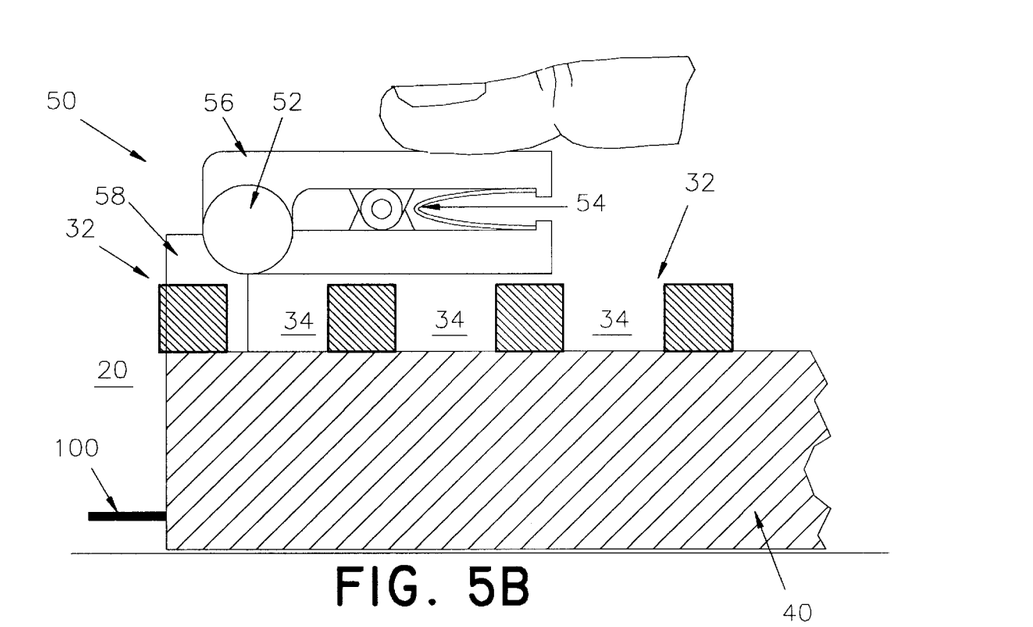
FIG. 5B is a side view of the adjustable lock of FIG. 5A, illustrating the lock in a disengaged position.

The adjustable lock 50 shown in FIGS. 5A–B utilizes a hinge mechanism 202. As shown in FIG. 5A, the elastic spring tension member 54 is positioned such that it normally biases the engagement member 52 within the stop positions 34 between the stops 32, thereby removably locking the extension member 40 and electrode blade 48 in a desired position. As shown in FIG. 5B, when the adjustment tab 56 is depressed sufficiently against the biasing force of the tension member 54, the engagement member 52 rotates about hinge 202, thereby disengaging the engagement member 52 from the stops 32. With the engagement member disengaged, the surgeon using the invention 1 can slide adjustment tab 56 up or down in the channel 30 to adjust the electrode blade 48 to a desired position. Once a desired position has been selected, the surgeon releases the force on the tension member 54, and the tension member then bias the engagement member 52 within a stop position 34, thereby removably locking the extension member 40 and the electrode blade 48 in the desired position.

Figure 6A:
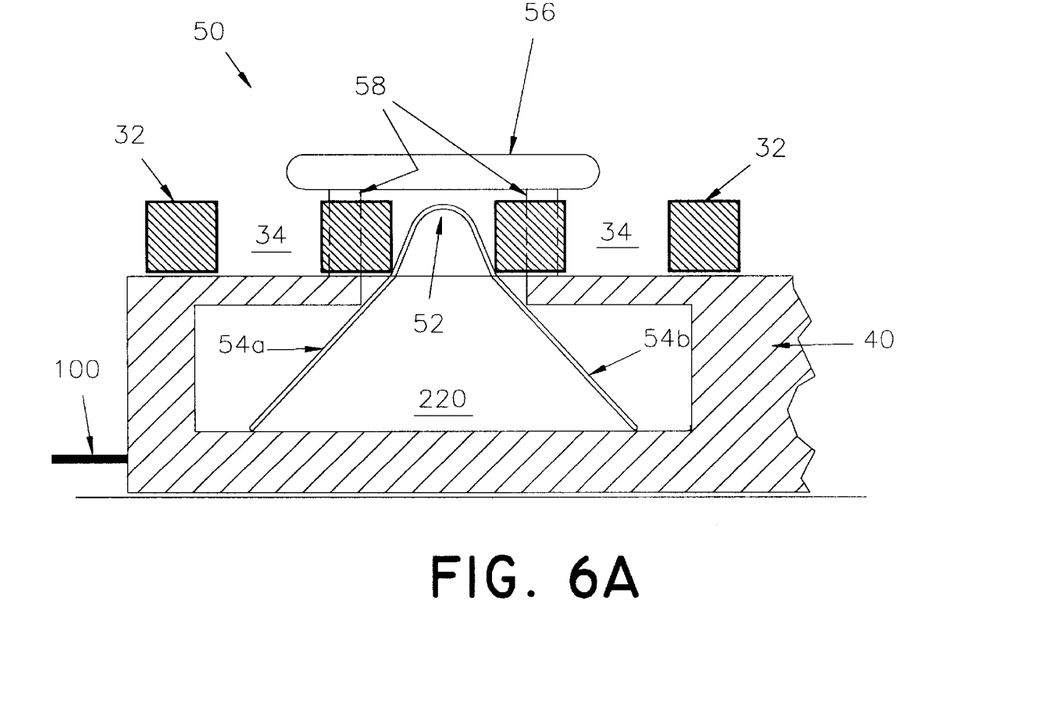
FIG. 6A is a side view of one embodiment of an adjustable lock component of the invention, illustrating the lock in an engaged position.
Figure 6B:
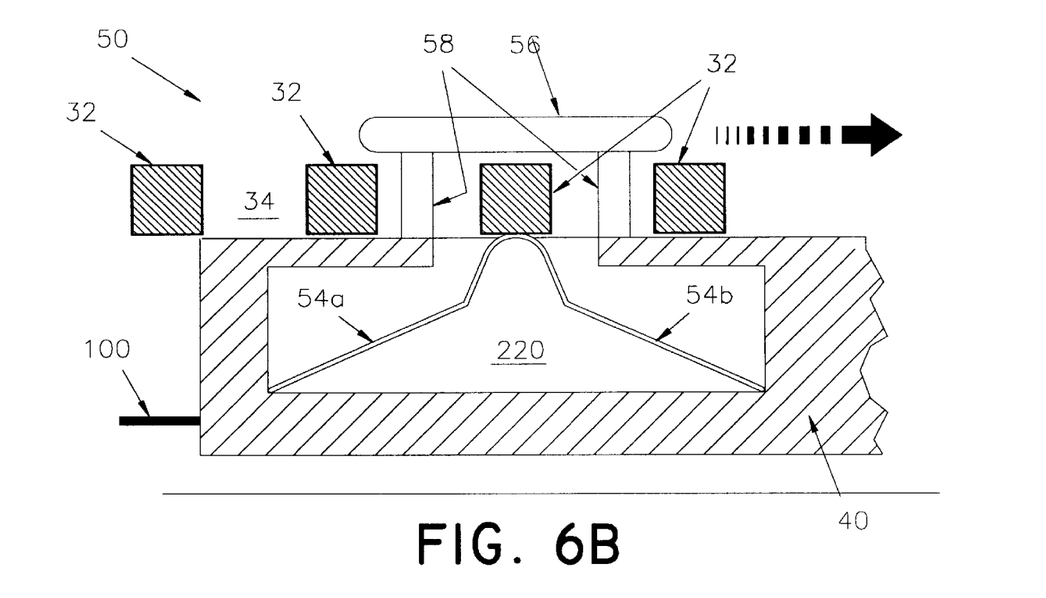
FIG. 6B is a side view of the adjustable lock of FIG. 6A, illustrating the lock in a disengaged position.

The adjustable lock 50 shown in FIGS. 6A–B utilizes a metal strip 54 as both the tension member 54 and the engagement member 52. The extension member 40 has a cavity 220 within which the tension member 54 can expand when under an external force during adjustment. FIGS. 6A and 6B show a side view of the metal strip 54 positioned in the cavity 220 of the extension member 40. As can be seen in FIG. 6A, the metal strip is configured such that it has an engagement member 52 which extends downward into arms 54a and 54b, which comprise the tension member 54. As shown in FIG. 6A, when not under an external force during adjustment, the tension member 54 forces engagement member 52 to protrude through an opening in extension member 40. The tension member 54 thus normally biases the engagement member 52 within the stop positions 34 between the stops 32, thereby removably locking the extension member 40 and electrode blade 48 in a desired position. As shown in FIG. 6B, when an external sliding force is applied to adjustment tab 56, the arms 54a and 54b of the tension member 54 are forced downward and outward within cavity 220, while engagement member 52 slides underneath the adjoining stop 32. As shown in FIG. 6A, when the engagement member 52 passes into a new stop position 34, the elastic tension in tension member 54 causes engagement member 52 to enter the stop position 34 and engage the stops 32, thereby removably locking the extension member 40 and the electrode blade 48 in the new stop position 34.

Figure 7A:
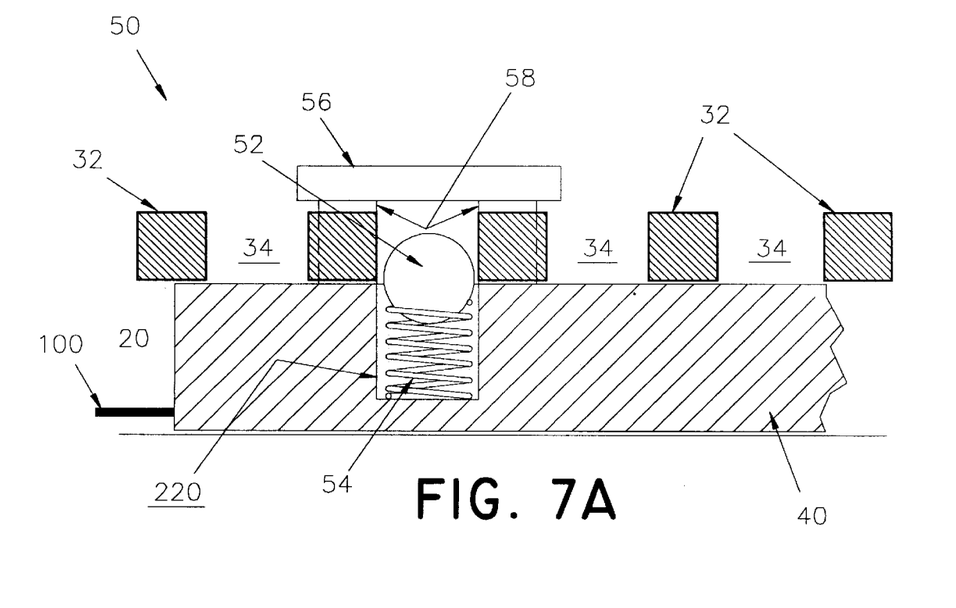
FIG. 7A is a side view of one embodiment of an adjustable lock component of the invention, illustrating the lock in an engaged position.
Figure 7B:
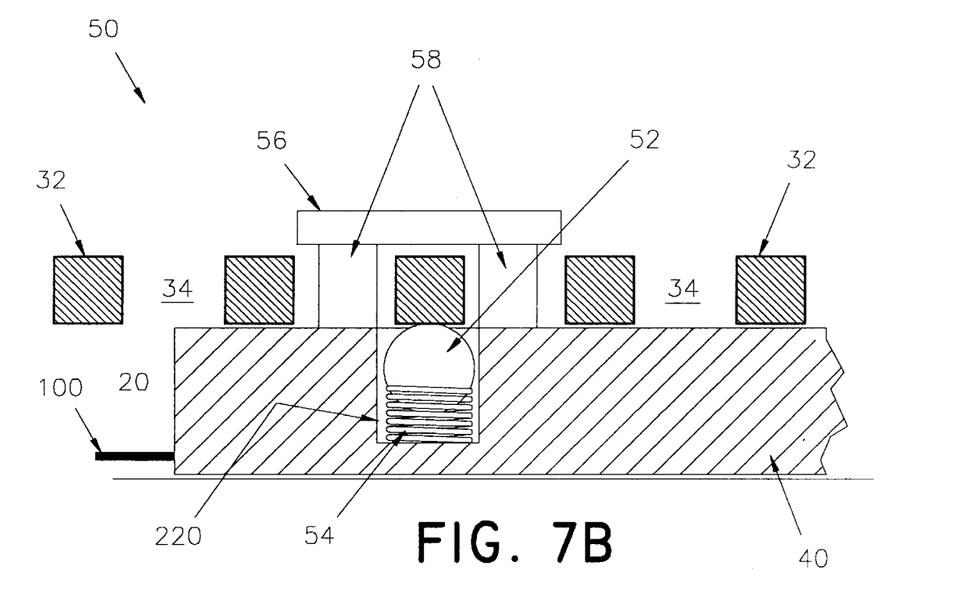
FIG. 7B is a side view of the adjustable lock of FIG. 7A, illustrating the lock in a disengaged position.

The adjustable lock 50 shown in FIGS. 7A–B utilizes a spring 54 as the tension member 54 and a bearing 52 as the engagement member 52. The tension member 54 is positioned in a cavity 220 in extension member 40. As shown in FIG. 7A, when not under an external force during adjustment, the tension member 54 forces engagement member 52 to protrude through an opening in extension member 40. The tension member 54 thus normally biases the engagement member 52 within the stop positions 34 between the stops 32, thereby removably locking the extension member 40 and the electrode blade 48 in a desired position. As shown in FIG. 7B, when an external sliding force is applied to adjustment tab 56, the tension member 54 compresses within the extension member 40, allowing engagement member 52 to slide underneath the adjoining stop 32. As shown in FIG. 7A, when the engagement member 52 passes into a new stop position 34, the elastic tension in tension member 54 causes engagement member 52 to enter the stop position 34 and engage the stops 32, thereby removably locking the extension member 40 and the electrode blade 48 in the new stop position 34.

Figure 8A:
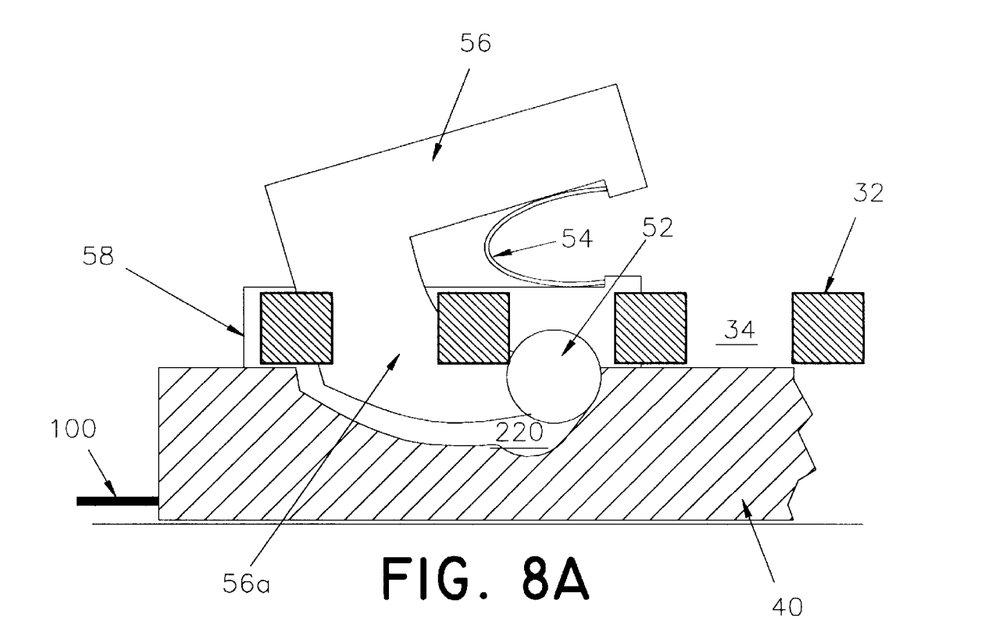
FIG. 8A is a side view of one embodiment of an adjustable lock component of the invention, illustrating the lock in an engaged position.
Figure 8B:
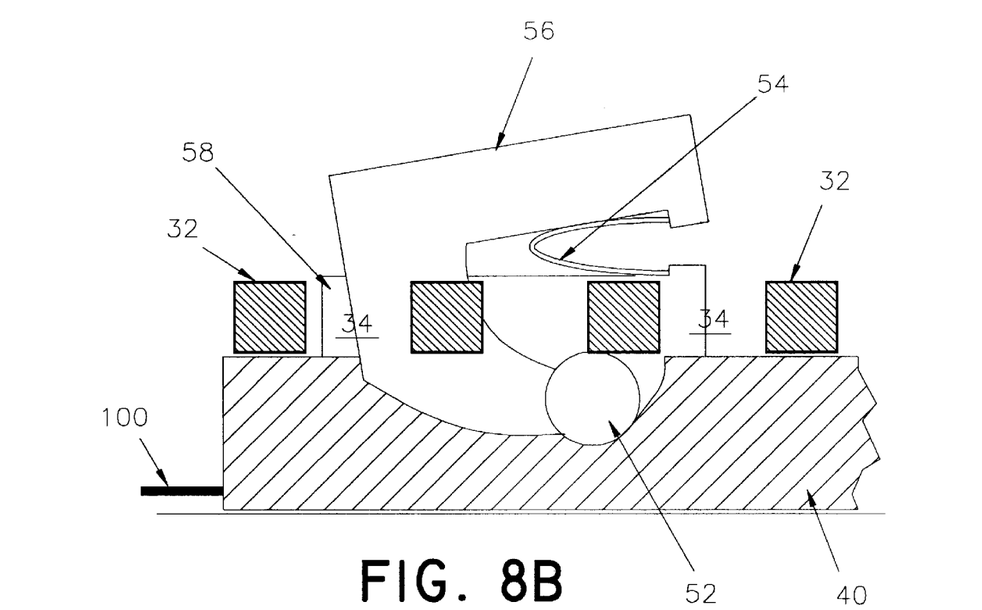
FIG. 8B is a side view of the adjustable lock of FIG. 8A, illustrating the lock in a disengaged position.

The adjustable lock 50 shown in FIGS. 8A–B utilizes a depressible adjustment tab 56 which has a descending portion 56a. Engagement member 52 is formed on the end of the descending portion 56a. The extension member is provided with a cavity 220 for permitting depression of the adjustable lock 50. The tension member can be a spring or strip of metal positioned so as to normally bias the engagement member 52 in a stop position 34. As shown in FIG. 8A, when not under an external force during adjustment, the tension member 54 forces engagement member 52 to partially protrude through an opening in extension member 40. The tension member 54 thus normally biases the engagement member 52 within the stop positions 34 between the stops 32, thereby removably locking the extension member 40 and the electrode blade 48 in a desired position. As shown in FIG. 8B, when an external force is applied to adjustment tab 56, the tension member 54 compresses, allowing engagement member 52 to slide underneath the adjoining stop 32. As shown in FIG. 8A, when the engagement member 52 passes into a new stop position 34, the elastic tension in tension member 54 causes engagement member 52 to enter the stop position 34 and engage the stops 32, thereby removably locking the extension member 40 and the electrode blade 48 in the new stop position 34.

Figure 9A:
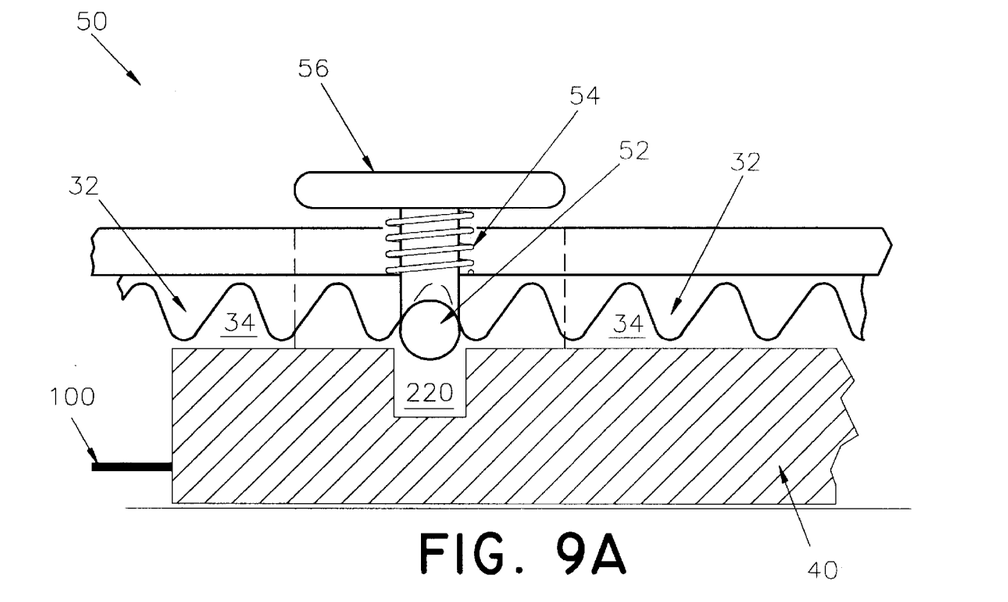
FIG. 9A is a side view of one embodiment of an adjustable lock component of the invention, illustrating the lock in an engaged position.
Figure 9B:
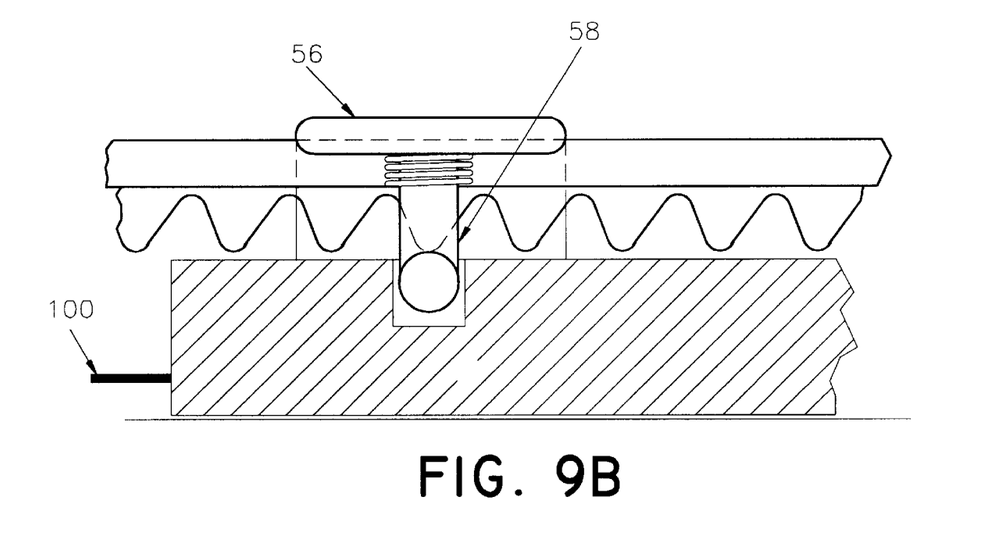
FIG. 9B is a side view of the adjustable lock of FIG. 9A, illustrating the lock in a disengaged position.

FIGS. 9A–B show an adjustable lock which is similar to the mechanism shown in FIGS. 8A–B. The adjustment tab can be depressed to disengage the engagement member 52 from the stops 32. However, the stops 32 are a series of projections 32 positioned on an inner surface of the elongated body 10 on either side of the channel 30. The configuration of stops 32 shown in FIGS. 9A–B can also be used with the adjustable lock mechanisms shown in FIGS. 5–8.

Figure 3:
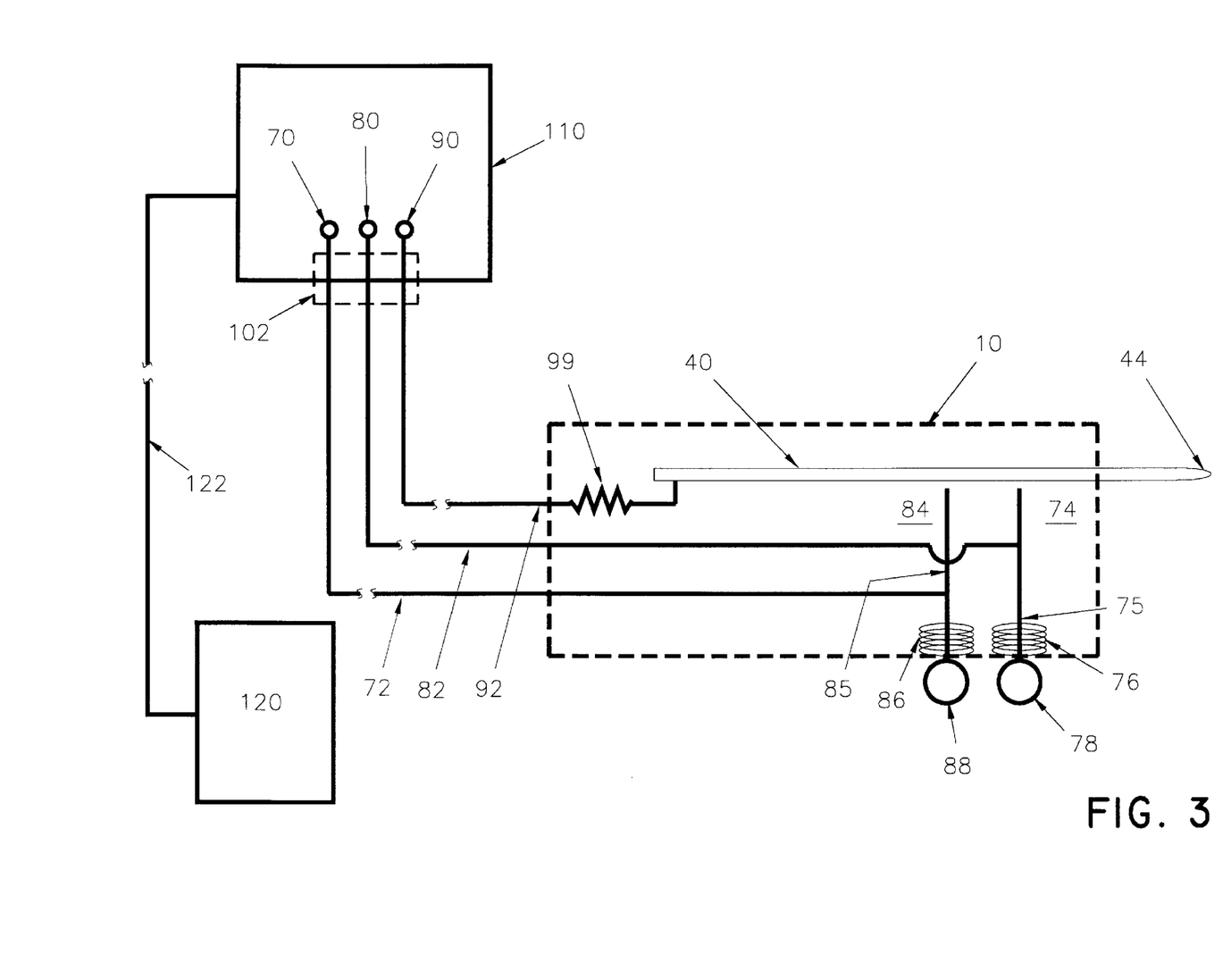
FIG. 3 is a schematic view of electrical components of one embodiment of the invention.
Figure 4:
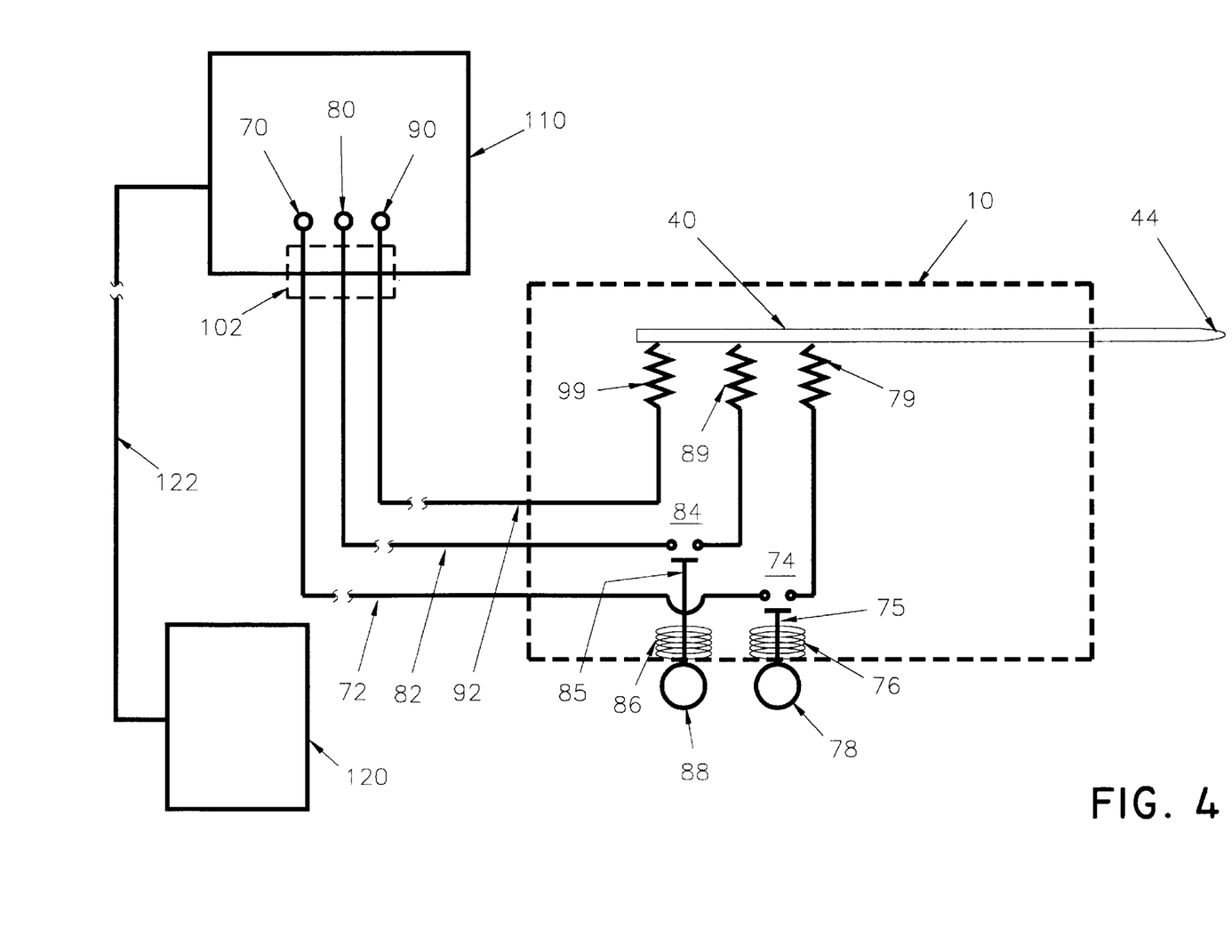
FIG. 4 is a schematic view of electrical components of one embodiment of the invention.

The electrical components of the invention 1 are similar to those used on conventional electrocautery surgical scalpels, but have been modified to accommodate the extension and retraction of the electrode blade 48. FIGS. 3 and 4 provide schematic views of two preferred embodiments of the electrical components of the invention 1. The invention 1 is powered by a commercially available electrosurgical generator/cautery unit 110 of the type widely used on conventional electrocautery surgical scalpels. The electrosurgical generator 110 has a coagulation switching terminal 70, a cut switching terminal 80, and an electrical power terminal 90. The generator 110 produces an electrosurgical coagulation current at the electrical power terminal 90 when the coagulation switching terminal 70 is electrically connected to the electrical power terminal 90. The generator 110 produces an electrosurgical cutting current at the electrical power terminal 90 when the cut switching terminal 80 is electrically connected to the electrical power terminal 90. Accordingly, the invention 1 is provided with electrical components, as shown schematically in FIGS. 3 and 4, for electrically connecting the coagulation switching terminal 70 of the generator 110 to the electrical power terminal 90, and for electrically connecting the cut switching terminal 80 of the generator 110 to the electrical power terminal 90 of the generator 110.

A coagulation switching conductor 72, a cut switching conductor 82, and an electric power conductor 92 preferably extend from the upper end 12 of the body 10, and are preferably bundled together in an electric cable 100. The electric cable 100 has a standard electrical connector or plug 102 for electrically coupling the coagulation switching conductor 72, the cut switching conductor 82, and the electric power conductor 92 to a jack (not shown) on the electrosurgical generator 110, in a manner well known to those of ordinary skill in the art.

As shown in FIGS. 3 and 4, a manual coagulation switch means 74 is mounted on the body 10 and is electrically connected to the electrical power conductor 92, the coagulation switching conductor 72, and a coagulation switch actuating means 75. A biasing means 76 is provided for holding coagulation switch 74 in an open position when electrosurgical coagulation current is not required. The coagulation switch actuation means 75 is provided with a coagulation button 78. When a surgeon using the invention desires electrosurgical coagulation current, he or she depresses the coagulation button 78, thereby closing the coagulation switch 74. With the coagulation switch 74 closed, the coagulation switching terminal 70 of generator 110 is brought into electrical contact with the electrical power terminal 90 of the generator 110, and the generator 110 produces an electrosurgical coagulation current at the electrical power terminal 90. The electrosurgical coagulation current is delivered to the electrode blade 48. When the lower end 49 of the blade 48 is brought into contact with the tissue of a patient, the electrosurgical current coagulates the tissue.

As shown in FIGS. 3 and 4, a manual cut switch means 84 is mounted on the body 10 and is electrically connected to the electrical power conductor 92, the cut switching conductor 82, and a cut switch actuating means 75. A biasing means 86 is provided for holding cut switch 84 in an open position when electrosurgical cut current is not required. The cut switch actuation means 85 is provided with a cut button 88. When a surgeon using the invention desires electrosurgical cut current, he or she depresses the cut button 88, thereby closing the cut switch 84. With the cut switch 84 closed, the cut switching terminal 80 of generator 110 is brought into electrical contact with the electrical power terminal 90 of the generator 110, and the generator 110 produces an electrosurgical cut current at the electrical power terminal 90. The electrosurgical cut current is delivered to the electrode blade 48. When the lower end 49 of the blade 48 is brought into contact with the tissue of a patient, the electrosurgical current cuts the tissue.

The switch mechanisms comprising components 74–79 and 84–89 can be of any of the types of switch mechanisms presently used on electrosurgical devices, such as snap switches, slide switches, breaker switches, and the like. The switch can also be a blended current switch which causes the electrosurgical generator to produce a blended current. Additionally, a foot pedal can be used in place of a finger operated switch, in a manner well known to those of ordinary skill in the art.

The electrosurgical current applied to the patient through the electrode blade 48 is returned to the generator 110 by a dispersive electrode 120. The dispersive electrode is electrically connected to the generator 110 by a cable 122. The dispersive electrode 120 is applied to the skin of the patient being operated on. The dispersive electrode 120 is relatively large in area in order to keep the current density in the region of the dispersive electrode 120 low, and thereby prevent tissue damage in the area of the dispersive electrode 120. Current is returned from the dispersive electrode 120 to the generator 110 by the cable 122.

Because the coagulation switching conductor 72, cut switching conductor 82, and electric power conductor 92 must be able to selectively make electrical contact with the extendable and retractable electrode blade 48 throughout the range of motion of the blade 48, these components are equipped with certain features which allow them to remain in selective electrical contact with the electrode blade 48 between maximally retracted and maximally extended positions of the electrode blade 48.

One such embodiment is shown schematically in FIG. 3. As seen in FIG. 3, one end of the electric power conductor 92 is provided with a slack portion 99 located inside of elongated body 10 and affixed to electrode blade 48. The slack portion 99 of the electric power conductor 92 allows the electric power conductor 92 to remain in electrical contact with electrode blade 48 through the range of motion of electrode blade 48. In the embodiment depicted in FIG. 3, coagulation switch actuating means 75 and cut switch actuating means 85 complete the respective coagulation or cut electrical circuit by making selective direct contact with electrode blade 48, thereby closing switch 74 or 84, respectively. When button 78 or 88 is depressed by the surgeon, the respective switch actuating means 75 or 85 is brought into direct contact with the electrode blade 48, thereby completing the circuit.

A second embodiment is shown schematically in FIG. 4. As seen in FIG. 3, one end of the electric power conductor 92 is provided with a slack portion 99 located inside of elongated body 10 and affixed to electrode blade 48. A coagulation slack lead 79 and a cut slack lead 89 are also provided. The coagulation slack lead 79 is electrically coupled to the coagulation switch 74, while the cut slack lead 89 is electrically coupled to the cut switch 84. Both slack leads 79 and 89 are positioned inside of the elongated body 10. The slack portion 99 of the electric power conductor 92 allows the electric power conductor 92 to remain in electrical contact with electrode blade 48 through the range of motion of electrode blade 48. Additionally, because coagulation slack lead 79 is electrically coupled to the electrode blade 48 throughout the range of motion of the electrode blade 48, the coagulation circuit can be completed by depressing coagulation button 78, thereby causing biasing means 76 to close the coagulation switch 74. Likewise, because cut slack lead 89 is electrically coupled to the electrode blade 88 throughout the range of motion of the electrode blade 48, the cut circuit can be completed by depressing cut button 88, thereby causing biasing means 86 to close the cut switch 84.

When a conventional foot pedal is used, the coagulation and cut currents are regulated by mechanisms external to the electrocautery surgical instrument. Accordingly, the various electrical components, with the exception of the coagulation switching conductor 72, the cut switching conductor 82, and the power conductor 92, can be eliminated from the elongated body of the invention 1. In this embodiment, coagulation switching conductor 72, the cut switching conductor 82, and the power conductor 92 (which will generally be bundled together in a single cable) can simply slide up and down in the internal track 20 as extension member 40 is manipulated up and down.

The adjustable electrocautery surgical apparatus I can be combined with a vacuum for suctioning of blood and coagulation, as has been discussed in other patents. See e.g. U.S. Pat. No. 5,318,565.

In operation during surgery, the adjustable electrocautery surgical apparatus 1 of the invention is used to perform surgical procedures in the manner of a conventional electrosurgical tool. However, when the surgeon desires a longer or shorter electrode blade 48, the surgeon simply uses a finger or thumb to apply pressure to the adjustment tab 56. The force applied by the surgeon's thumb or finger disengages the engagement member 52 from the stops 32 and from a stop position 34. The surgeon then continues to apply pressure to slide the adjustment tab 56 up or down, as desired, thereby adjusting the length of the electrode blade 48 to a desired length. When the electrode blade 48 has been adjusted to a desired length, the surgeon releases pressure on the adjustment tab 56, whereupon the tension means 54 returns the engagement member 52 to the selected stop position 34. With the electrode blade 48 thus removably locked in the newly selected stop position 34, the surgeon then continues to use the electrosurgical tool of the invention 1 in the conventional manner to proceed with the surgical procedure.

Although the present invention has been described in terms of specific embodiments, it is anticipated that alterations and modifications thereof will no doubt become apparent to those skilled in the art. It is therefore intended that the following claims be interpreted as covering all such alterations and modifications that fall within the true spirit and scope of the invention.

I claim:

1. An adjustable electrocautery surgical apparatus for selectively delivering electrosurgical coagulation and cut current from an electrosurgical generator to a surgical site comprising:

an elongated body member having a lower end and an upper end, said elongated body member having a longitudinal channel passing through a sidewall thereof, a plurality of stops in said channel for providing a sequence of stop positions between maximally retracted and maximally extended positions of said apparatus, a track disposed longitudinally in said elongated body, said track positioned substantially parallel to said channel, an elongated extension member slidably disposed in said track, an electrode blade extending from a lower end of said extension member, an exposed lower end of said electrode blade extending from said lower end of said elongated body, an adjustable lock on said extension member, said adjustable lock slidably positioned in said longitudinal channel of said elongated body member so as to selectively engage said stops and thereby lock said electrode blade in a selected stop position between said maximally retracted and said maximally extended positions, and a means for electrically coupling said electrode blade to the coagulation current of the electrosurgical generator and means for electrically coupling said electrode blade to the cut current of the electrosurgical generator, such that coagulation or cut current, or a combination thereof, can be selectively delivered to said electrode blade.

2. The apparatus of claim 1, wherein said adjustable lock comprises an engagement member for engaging said stops, a tension member for normally biasing said engagement member in a stop position, an adjustment tab for selectively disengaging said engagement member from said stops, and a guide member disposed at least partially in said channel and fixedly coupled to said adjustment tab and said extension member, such that sliding said adjustment tab causes said extension member to slide in said track to thereby selectively adjust said electrode blade between maximally extended and maximally retracted positions.

3. The apparatus of claim 2, wherein said engagement member is on said adjustment tab, said adjustment tab is hinged to said guide member, and said tension member is positioned between said adjustment tab and said guide member so as to normally bias said engagement member in one of said stop positions.

4. The apparatus of claim 2, wherein said extension member further comprises a cavity therein, said engagement member and said tension member are configured from a metal strip, said tension portion of said metal strip disposed in said cavity, and said engagement member portion of said metal strip normally biased to protrude from an opening in said extension member so as to engage one of said stop positions.

5. The apparatus of claim 2, wherein said extension member further has a cavity therein, said tension member is a spring positioned in said cavity, and said engagement member is a bearing, said bearing positioned on said spring so as to normally bias said bearing in one of said stop positions.

6. The apparatus of claim 2, wherein said extension member further has a cavity therein, said engagement member is formed on a descending portion of said adjustment tab, said engagement member is positioned in said cavity of said extension member, and said tension member is positioned between said adjustment tab and said guide member so as to normally bias said engagement member in one of said stop positions.

7. The apparatus of claim 1, wherein said stops are portioned in pairs on opposite sides of said channel.

8. The apparatus of claim 1, wherein said stops are positioned on an inner surface of said elongated body on either side of said channel.

9. The apparatus of claim 1, wherein said means for electrically coupling said electrode blade to the coagulation current of the electrosurgical generator further includes a coagulation circuit in said elongated body for selectively delivering coagulation current from said electrosurgical generator to said electrode blade, and said means for electrically coupling said electrode blade to the cut current of the electrosurgical generator further includes a cut circuit in said elongated body for selectively delivering cut current from said electrosurgical generator to said electrode blade.

10. The apparatus of claim 9, wherein said means for electrically coupling includes an electrical cord extending from said elongated body, said cord having an electric power conductor for electrically coupling with an electric power terminal of the electrosurgical generator, a coagulation switching conductor for electrically coupling with a coagulation switching terminal of the electrosurgical generator, and a cutting switching conductor for electrically coupling with a cutting switching terminal of the electrosurgical generator, said electric power conductor affixed to said electrode blade via a slack portion, said slack portion allowing said electric power conductor to remain in contact with said electrode blade throughout said range of adjustment of said electrode blade, said coagulation circuit including a coagulation switch actuating means electrically coupled to said coagulation switching conductor, a biasing means for holding said coagulation switch actuating means in an open switch position when coagulation current is not required, and an external button for depressing said coagulation switch actuating means into contact with said electrode blade, to thereby close said coagulation circuit and selectively deliver electrosurgical coagulation current from said electrosurgical generator to said electrode blade, and said cut circuit including a cut switch actuating means electrically coupled to said cut switching conductor, a biasing means for holding said cut switch actuating means in an open switch position when cut current is not required, and an external button for depressing said cut switch actuating means into contact with said electrode blade, to thereby close said cut circuit and selectively deliver electrosurgical cut current from said electrosurgical generator to said electrode blade.

11. The apparatus of claim 9, wherein said means for electrically coupling includes an electrical cord extending from said elongated body, said cord having an electric power conductor for electrically coupling with an electric power terminal of the electrosurgical generator, a coagulation switching conductor for electrically coupling with a coagulation switching terminal of the electrosurgical generator, and a cutting switching conductor for electrically coupling with a cutting switching terminal of the electrosurgical generator, said electric power conductor affixed to said electrode blade via a slack portion, said slack portion allowing said electric power conductor to remain in contact with said electrode blade throughout said range of adjustment of said electrode blade, said coagulation circuit including a coagulation switch positioned between said coagulation switching conductor and a lead, said lead having a slack portion affixed to said electrode blade, said slack portion of said lead allowing said lead to remain in contact with said electrode blade throughout said range of adjustment of said electrode blade, a switch actuating means normally biased to open said coagulation switch, and an external button for closing said coagulation circuit to selectively deliver electrosurgical coagulation current from said electrosurgical generator to said electrode blade, and said cut circuit including a cut switch positioned between said cut switching conductor and a lead, said lead having a slack portion affixed to said electrode blade, said slack portion of said lead allowing said lead to remain in contact with said electrode blade throughout said range of adjustment of said electrode blade, a switch actuating means normally biased to open said cut switch, and an external button for closing said cut circuit to selectively deliver electrosurgical cut current from said electrosurgical generator to said electrode blade.

12. The apparatus of claim 10, wherein said adjustable lock comprises an engagement member for engaging said stops, a tension member for normally biasing said engagement member in a stop position, an adjustment tab for selectively disengaging said engagement member from said stops, and a guide member disposed at least partially in said channel and fixedly coupled to said adjustment tab and said extension member, such that sliding said adjustment tab causes said extension member to slide in said track to thereby selectively adjust said electrode blade between maximally extended and maximally retracted positions.

13. The apparatus of claim 12, wherein said engagement member is on said adjustment tab, said adjustment tab is hinged to said guide member, and said tension member is positioned between said adjustment tab and said guide member so as to normally bias said engagement member in one of said stop positions.

14. The apparatus of claim 12, wherein said extension member further comprises a cavity therein, said engagement member and said tension member are configured from a metal strip, said tension portion of said metal strip disposed in said cavity, and said engagement member portion of said metal strip normally biased to protrude from an opening in said extension member so as to engage one of said stop positions.

15. The apparatus of claim 12, wherein said extension member further has a cavity therein, said tension member is a spring positioned in said cavity, and said engagement member is a bearing, said bearing positioned on said spring so as to normally bias said bearing in one of said stop positions.

16. The apparatus of claim 12, wherein said extension member further has a cavity therein, said engagement member is formed on a descending portion of said adjustment tab, said engagement member is positioned in said cavity of said extension member, and said tension member is positioned between said adjustment tab and said guide member so as to normally bias said engagement member in one of said stop positions.

17. The apparatus of claim 11, wherein said adjustable lock comprises an engagement member for engaging said stops, a tension member for normally biasing said engagement member in a stop position, an adjustment tab for selectively disengaging said engagement member from said stops, and a guide member disposed at least partially in said channel and fixedly coupled to said adjustment tab and said extension member, such that sliding said adjustment tab causes said extension member to slide in said track to thereby selectively adjust said electrode blade between maximally extended and maximally retracted positions.

18. The apparatus of claim 17, wherein said engagement member is on said adjustment tab, said adjustment tab is hinged to said guide member, and said tension member is positioned between said adjustment tab and said guide member so as to normally bias said engagement member in one of said stop positions.

19. The apparatus of claim 17, wherein said extension member further comprises a cavity therein, said engagement member and said tension member are configured from a metal strip, said tension portion of said metal strip disposed in said cavity, and said engagement member portion of said metal strip normally biased to protrude from an opening in said extension member so as to engage one of said stop positions.

20. The apparatus of claim 17, wherein said extension member further has a cavity therein, said tension member is a spring positioned in said cavity, and said engagement member is a bearing, said bearing positioned on said spring so as to normally bias said bearing in one of said stop positions.

21. The apparatus of claim 17, wherein said extension member further has a cavity therein, said engagement member is formed on a descending portion of said adjustment tab, said engagement member is positioned in said cavity of said extension member, and said tension member is positioned between said adjustment tab and said guide member so as to normally bias said engagement member in one of said stop positions.

22. The apparatus of claim 9, wherein said stops are portioned in pairs on opposite sides of said channel.

23. The apparatus of claim 9, wherein said stops are positioned on an inner surface of said elongated body on either side of said channel.

* * * * *